United States Patent [19]

Narfström

[11] Patent Number: 5,790,996
[45] Date of Patent: Aug. 11, 1998

[54] EXAMINATION TABLE FOR SUPPORTING AND POSITIONING A PATIENT IN A MEDICAL EXAMINATION APPARATUS

[75] Inventor: Jan Narfström, Sollentuna, Sweden

[73] Assignee: Siemens-Elma AB, Solna, Sweden

[21] Appl. No.: 936,996

[22] Filed: Sep. 25, 1997

[30] Foreign Application Priority Data

Sep. 27, 1996 [SE] Sweden .......................... 9603535

[51] Int. Cl.$^6$ .......................... A61G 13/04; A61B 6/04
[52] U.S. Cl. .......................... 5/610; 5/601; 108/6; 378/209
[58] Field of Search .......................... 5/601, 610, 943, 5/600; 108/6; 378/209

[56] References Cited

U.S. PATENT DOCUMENTS

| | | | |
|---|---|---|---|
| 2,775,496 | 12/1956 | Berggren | 5/601 |
| 4,618,133 | 10/1986 | Siczek | 5/610 |
| 4,697,802 | 10/1987 | Brendl et al. | 5/601 |
| 5,361,436 | 11/1994 | Hahn | 5/610 |
| 5,572,569 | 11/1996 | Benoit et al. | 5/610 |

OTHER PUBLICATIONS

Siemens Brochure for Coroskop T.O.P./Bicor T.O.P.
Siemens Brochure for Koordinat Angio.

Primary Examiner—Alexander Grosz
Attorney, Agent, or Firm—Hill & Simpson

[57] ABSTRACT

An examination table for supporting a patient in a medical examination apparatus has a positioning plate and a floor stand, the positioning plate being adjustable in height and able to be tilted. The examination table is very simple and space-saving in construction, but still allows a tilting of the positioning plate into a vertical position, by virtue of the floor stand having a curved girder which has a base end at the floor fastened rotatably about a horizontal shaft, and the positioning plate is provided with a mount that is movably attached to the girder so that the mount with the positioning plate can be moved along the longitudinal direction of the girder.

5 Claims, 2 Drawing Sheets

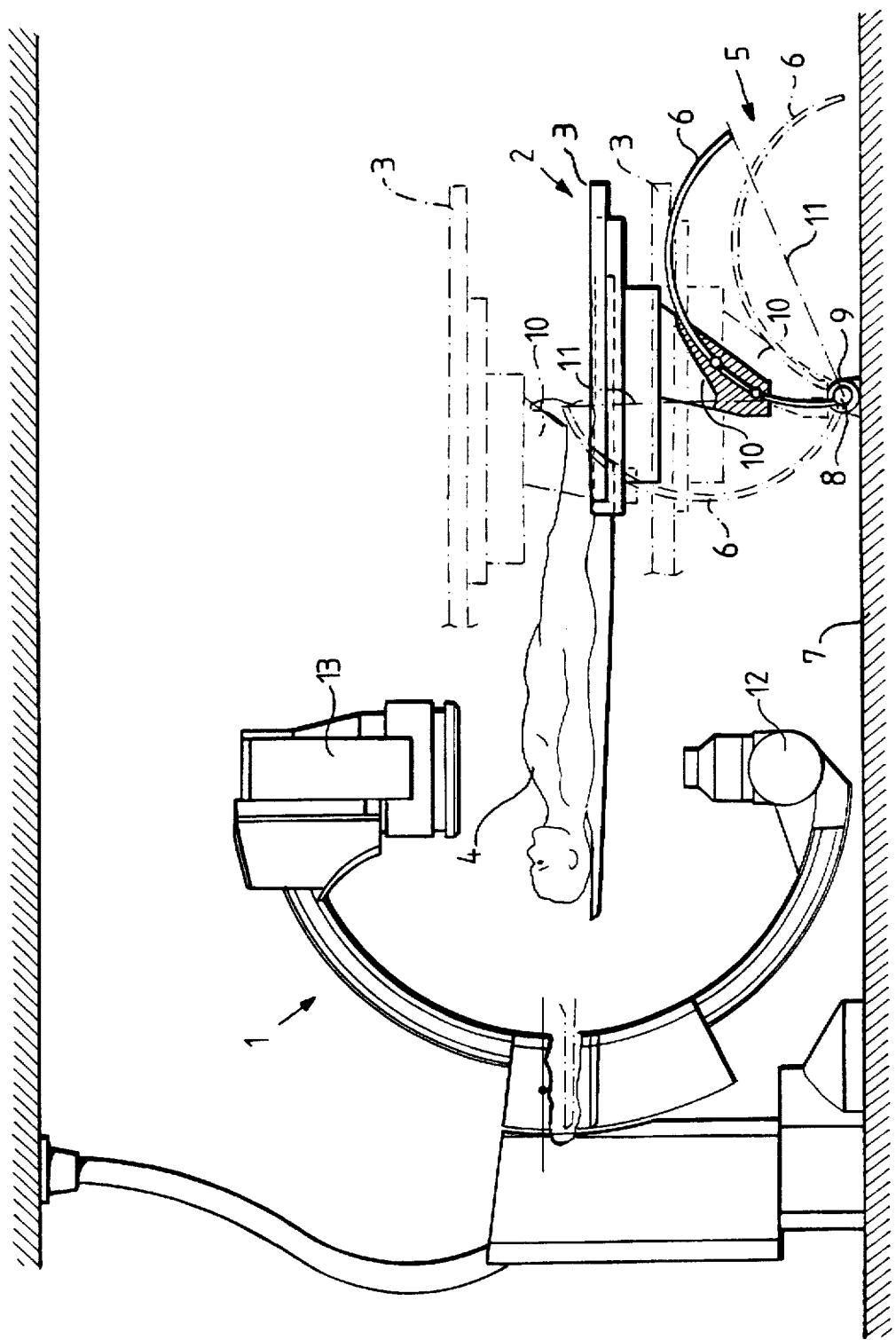

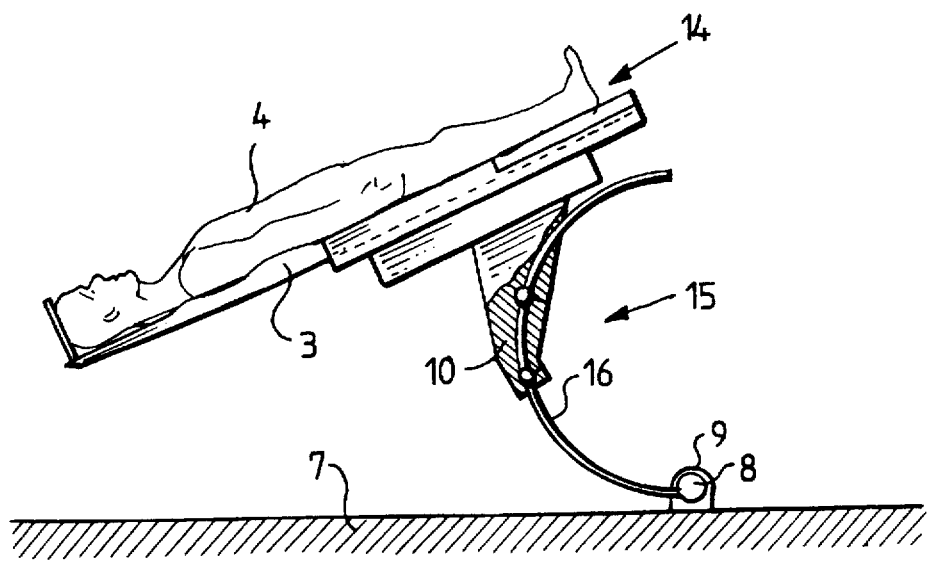
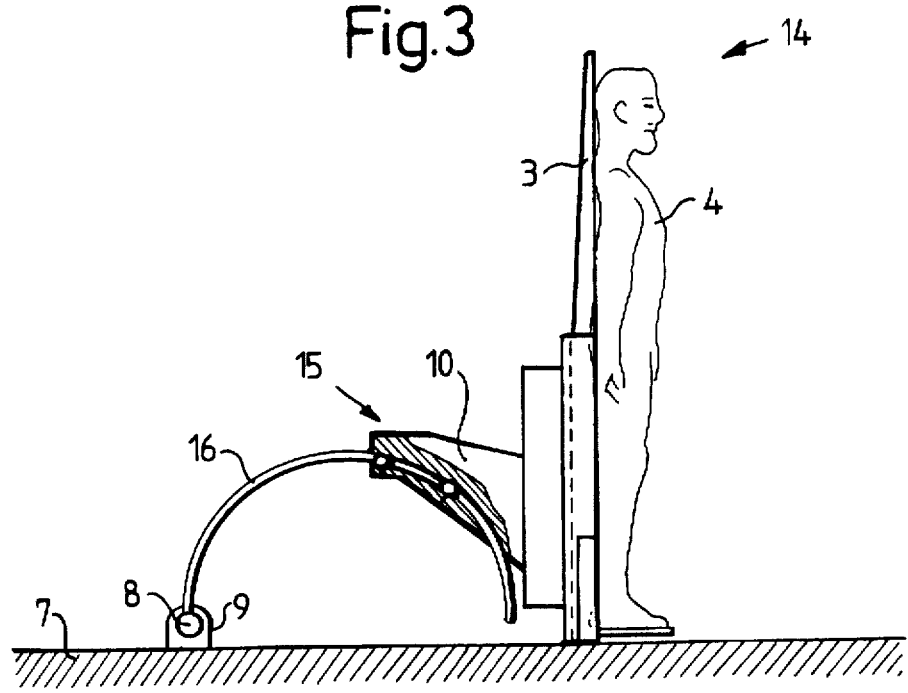

EXAMINATION TABLE FOR SUPPORTING AND POSITIONING A PATIENT IN A MEDICAL EXAMINATION APPARATUS

BACKGROUND OF THE INVENTION

FIELD OF THE INVENTION

The present invention relates to an examination table for positioning a patient in a medical examination apparatus, of the type having a positioning plate supported by a floor stand, the positioning plate being adjustable in height and able to be tilted.

DESCRIPTION OF THE PRIOR ART

It is of importance that the positioning plate in an examination table of this type be capable of being lowered in such a way that the patient can move onto and lie down on the positioning plate without difficulty, or can easily be transferred onto it from a gurney. The positioning plate then must be capable of being raised to a height that is acceptable for the physician and that is matched to the construction of the relevant component of the examination apparatus such as an X-ray stand. An examination table used in connection with X-ray examinations preferably also has a positioning plate that can be tilted, in particular in connection with contrast agent examinations, in which the contrast agent flows by means of gravity in the direction of the lowest point of the patient. A table that can be tilted can also be used if the patient is in a state of shock. The positioning plate can then be tilted rapidly into a position in which the patient's head reaches a low point. In this way, blood can flow rapidly to the head. In certain examinations, a tilting of the positioning plate with the patient thereon from a horizontal position into a vertical one is required. An example of such an examination is when, with the patient in a horizontal position, the physician inserts catheters into the patient using an X-ray installation, and applies them in position. After this, the positioning plate and patient are tilted into a vertical position. In this position, electrophysiological measurements are then carried out using an ECG installation. Such a vertical position is also useful in connection with certain leg vessel examinations.

An examination table of the type described above is known from the Siemens brochure "KOORDINAT ANGIO." The positioning table thereof rests on a fixed floor stand, including two telescoping columns arranged at a distance from one another, between which an X-ray film exchanger can be attached. When the height of the positioning plate is adjusted, the telescoping columns are moved synchronously, and when the plate is tilted one of the telescoping columns is raised in relation to the other. A tilting of the positioning plate into a vertical position is not possible with this examination table. In this examination table, the floor stand is relatively large and complicated in construction, causing the examination table to be relatively expensive to manufacture.

In U.S. Pat. No. 4,618,133, an X-ray examination table is described that can be tilted from a horizontal position into a vertical position. The floor stand has a frame construction that is relatively complicated, and is curved, and is provided with teeth, and can thus tilt in the way described above using motor-driven toothed wheels and chain transmissions. This known positioning plate, however, is not adjustable in height. Moreover, the floor stand extends over the entire length of the positioning plate, with the consequence that the examination table is space-consuming.

In German OS 4 229 318, an X-ray examination table is described having a positioning pete that is mounted so as to be pivoted about a fictitious fixed point in space. The examination table has a floor stand with a curved girder, the curve of which is oriented upwardly, and which can be moved in a mount attached to the floor and is rotatably attached with the positioning plate via a horizontal shaft. The girder is fashioned so that it runs underneath and parallel to the positioning plate, so that the positioning plate can be tilted only in the one direction. When the positioning plate is lowered, the girder is moved in such a way that it protrudes upwardly at one side of the mount, which can be disturbing. In addition, during a height adjustment the positioning plate is moved in its longitudinal direction.

SUMMARY OF THE INVENTION

An object of the invention is to provide an examination table of the general type described above with a floor stand that is extremely simple and space-saving in its construction, and which moreover permits a tilting of the positioning plate into a vertical position.

This object is inventively solved in an examination table having a floor stand formed by a curved girder which, at its base end near the floor, is rotatably fastened about a horizontal shaft, and having a positioning plate that is provided with a mount that is movably attached to the girder so that the mount with the positioning plate can be moved along the longitudinal direction of the girder (i.e., direction from the girder's base end to its opposite free end). By rotation of the girder about the horizontal axis at the same time that the mount with the positioning plate is moved along the longitudinal direction of the girder, the positioning plate can be adjusted in height and can be tilted all the way up to the point at which the plate assumes a vertical position.

In an embodiment of the inventive examination table, the girder has the shape of a half ellipse cut along its major axis, or has the shape of a part of this half ellipse. Due to the shape of the girder, the positioning plate can be lowered into a position that is advantageous for a patient to move onto the plate, and can be moved into a height position that is an optimal operating position for the physician.

The girder can alternatively have the shape of a circular arc segment with a sector angle up to 180°.

The positioning plate is preferably movable along its longitudinal direction relative to the mount.

DESCRIPTION OF THE DRAWINGS

FIG. 1 is a side elevational view of medical examination apparatus including an examination table constructed in accordance with the principles of the present invention, showing various positions which can be assumed by the examination table.

FIG. 2 is a side elevational view of a further embodiment of an examination table constructed in accordance with the principles of the present invention, shown in a tilted position.

FIG. 3 is a side elevational view of the embodiment of the examination table of FIG. 2, shown in a vertical, upright position.

DESCRIPTION OF THE PREFERRED EMBODIMENTS

FIG. 1 shows a medical examination system with an X-ray stand 1 and an examination table 2 according to the invention. The examination table 2 has a positioning plate 3, on which a patient 4 is positioned, and a floor stand 5. The floor stand 5 includes a curved girder 6, with a base end of the girder 6 at the floor being rotatably mounted about a horizontal shaft 8 that is connected to a motor 9. The positioning plate 3 is provided with a mount 10 in which the girder 6 is attached and is slidable. The girder 6 in this exemplary embodiment has the shape of a half ellipse, cut along the major axis 11. In FIG. 1, the large axis 11 is shown with a straight broken line. The positioning plate 3 is preferably also movable along its longitudinal direction relative to the mount 10.

The mount 10 with the positioning plate 3 has a channel therein through which the girder 6 extends, allowing the mount 10 to be moved along the longitudinal direction of the girder 6, using a motor, rollers and toothed belts, which are disposed in the channel of the mount 10. Displacement structures of this sort are known in connection with X-ray stands that have a C-shaped arm that is movably seated in a mount. An example of such an X-ray stand is known from the Siemens brochure "The fast and flexible new T.O.P.-Line Cardiac cath lab COROSKOP T.O.PIBICOR T.O.P".

FIG. 1 shows that the girder 6 is rotated about the shaft 8 using the motor 9, and the mount 10 on the girder 6 has been moved into a position in which the positioning plate 3 with the patient has reached a height position that is suited for an X-ray examination. FIG. 1 also shows that the positioning plate 3 has been moved in its longitudinal direction, using means that are known and thus need not be specified in more detail, into a position in which the chest of the patient comes to lie between the X-ray tube 12 and the image intensifier 13 of the X-ray stand 1. The position of the girder 6 (shown in broken lines in the FIG. 1), when this girder 6 has been rotated into a position in which the free end there of lies approximately against the floor 7, and in which the mount 10 (likewise shown in broken lines) on the girder has been moved in the direction of the shaft 8, produces a lowest position of the positioning plate 3. In FIG. 1, a broken-line position of the girder 6 is also shown in which the major axis 11 of the ellipse is approximately perpendicular to the floor 7, and the mount 10 has at the same time been moved upwardly on the girder 6. Here the positioning plate 3 has reached its highest position. A height displacement of the positioning plate 3 from a specified lowest position into a specified highest position, with a maintained vertical position, can be achieved by using the motor 9 to rotate the girder 6 about the shaft 8 at the same time that the mount 10 is moved in the longitudinal direction of the girder 6, using the aforementioned other motor (not shown). Apparatuses for controlling motors, as specified in this exemplary embodiment, are known from robotics technology, and thus need not be indicated in more detail herein.

FIG. 2 shows a further embodiment of an examination table 14 according to the invention. The examination table 14 differs from the examination table 2 shown in FIG. 1 only in that the floor stand 15 includes a girder 16 that comprises a circular arc segment with a sector angle of 180°. The sector angle can also be smaller than 180°. In other respects, the examination table 14 is constructed in the same way as the examination table 2 specified in detail in FIG. 1.

FIG. 2 shows that the girder 16 rotates about the shaft 8 by means of the motor 9, and the mount 10 as described above can be moved in the longitudinal direction of the girder 16 into a position in which the positioning plate 3 with the patient 4 is tilted forwards, so that the head of the patient 4 assumes a lowest position in relation to the body.

FIG. 3 shows that the girder 16 has been rotated about the shaft 8 by means of the motor 9 into a position in which the free end of the girder 16 lies fixedly on the floor 7, and the mount 10 has been moved into a position in which the positioning plate 3, and thus also the patient, has assumed a position that is approximately perpendicular to the floor.

The examination table 2 according to the invention in the embodiment of FIG. 1 also allows the positioning plate 3 to be positioned as shown in FIGS. 2 and 3, using the ellipse-shaped girder 6 and the mount 10. In addition, the ellipse-shaped girder 6 can be formed by only a part of this half ellipse, and accordingly does not have to be a complete half ellipse. In the same way, the examination table 14 can also be adjusted in height, as is specified in connection with the examination table 2 shown in FIG. 1. In addition, within the scope of the invention the positioning plate 3 can be moved in a specified way into further positions (not shown in the figures) in connection with different examinations, as desired by the physician. In sum, the invention provides an examination table that is very simple in construction and is thus relatively inexpensive to manufacture, and which is height-adjustable and can be tilted, and which is extremely space-saving due in particular to the shape and construction of the floor stand.

Although modifications and changes may be suggested by those skilled in the art, it is the intention of the inventor to embody within the patent warranted hereon all changes and modifications as reasonably and properly come within the scope of his contribution to the art.

I claim as my invention:

1. An examination table comprising:

a positioning plate being adjustable in height and able to be tilted;

a floor stand for supporting said positioning plate, said floor stand comprising a curved girder having a base end and a free end with a longitudinal extent of said girder extending between said base end and said free end, and a horizontal shaft adapted for rotatably fastening said base end of said curved girder to a floor; and a mount attached to said positioning plate and having a channel therein through which said girder extends for allowing movement of said mount along said longitudinal extent of said curved girder.

2. An examination table as claimed in claim 1 wherein said curved girder has a shape comprising a half of an ellipse cut along a major axis of said ellipse.

3. An examination table as claimed in claim 1 wherein said curved girder has a shape comprising portion or a half of an ellipse cut along a major axis of said ellipse.

4. An examination table as claimed in claim 1 wherein said girder has a shape comprising a circular arc segment having a segment angle less than or equal to 180°.

5. An examination table as claimed in claim 1 further comprising means for moving said positioning plate in a longitudinal direction of said positioning plane relative to said mount.

* * * * *